US006885006B2

United States Patent
Harrold et al.

(10) Patent No.: US 6,885,006 B2
(45) Date of Patent: Apr. 26, 2005

(54) ULTRAVIOLET SENSING OF THE CONDITION OF THE VANES AND BLADES OF GAS TURBINES IN SERVICE

(75) Inventors: Ronald T. Harrold, Murrysville, PA (US); Zal N. Sanjana, Mt. Lebanon, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 154 days.

(21) Appl. No.: 10/262,337

(22) Filed: Oct. 1, 2002

(65) Prior Publication Data

US 2003/0127602 A1 Jul. 10, 2003

Related U.S. Application Data

(60) Provisional application No. 60/326,478, filed on Oct. 1, 2001.

(51) Int. Cl.$^7$ .................................................. G01J 1/42
(52) U.S. Cl. ..................................... 250/372; 250/336.1
(58) Field of Search ............................... 250/372, 336.1

(56) References Cited

U.S. PATENT DOCUMENTS

| | | |
|---|---|---|
| 5,532,479 A | 7/1996 | Jung |
| 5,544,478 A | 8/1996 | Shu et al. |
| 5,557,099 A | 9/1996 | Zielinski et al. |
| 5,570,186 A | 10/1996 | Satzger et al. |
| 6,037,581 A | 3/2000 | Zorner |
| 6,080,982 A | 6/2000 | Cohen |
| 6,094,989 A | 8/2000 | Twerdochlib |
| 6,172,752 B1 | 1/2001 | Haruna et al. |
| 6,261,226 B1 * | 7/2001 | McKenna et al. .......... 600/109 |
| 6,320,184 B1 | 11/2001 | Winklhofer et al. |
| 6,323,491 B1 * | 11/2001 | Forsyth ..................... 250/372 |
| 6,341,936 B1 | 1/2002 | Cowie et al. |
| 6,644,917 B1 * | 11/2003 | Zhao et al. ................. 415/200 |
| 2003/0115941 A1 * | 6/2003 | Srivastava et al. ......... 73/118.1 |

OTHER PUBLICATIONS

Liebert, "Phosphors Light Way to Longer Life," 2003, Modern Power Systems, Volumne 23, pp. 1–2.*

* cited by examiner

*Primary Examiner*—David Porta
*Assistant Examiner*—Christine Sung

(57) ABSTRACT

A method and apparatus for monitoring the condition of the thermal barrier coating on turbine blades and vanes is provided. The coating is monitored with ultraviolet sensors which can detect ultraviolet radiation emitted from electrical discharges and glow coronas at the surface of the blades and vanes. Such electrical glow discharges and coronas are the result of friction electricity found at the surface of blades and vanes, and are also due to the high pressure, temperature and velocity conditions within the turbine. As the thermal barrier coating deteriorates, the electrical discharges and glow coronas and associated UV emissions decrease in magnitude or have other characteristic changes, thus permitting monitoring of the corona to detect changes in the coating over time.

6 Claims, 3 Drawing Sheets

PRESSURE-SPACING DEPENDENCE OF THE DIELECTRIC STRENGTH
OF GASES. [PASCHEN'S CURVES]

ULTRAVIOLET SENSING OF THE CONDITION OF THE VANES AND BLADES OF GAS TURBINES IN SERVICE

CROSS-REFERENCE TO RELATED APPLICATIONS

This application claims priority under 35 U.S.C. §119(e) to provisional application Ser. No. 60/326,478, filed Oct. 1, 2001.

FIELD OF THE INVENTION

The present invention provides a method and apparatus for monitoring the condition of the thermal barrier coating on turbine blades and vanes. Specifically, the coating can be monitored with ultraviolet sensors that detect ultraviolet radiation emitted from electrical discharges (sparks) and glow coronas at the surface of the blades and vanes. As the thermal barrier coating deteriorates, electrical discharges and the associated ultraviolet emissions decrease, thus permitting monitoring of the emissions to detect changes in the coating over time.

BACKGROUND INFORMATION

The blades and vanes of gas turbine machines operate in an extremely harsh environment with high gas pressures and velocities and temperatures around 1300° C. In order to withstand this environment, the blades and vanes in a combustion turbine are made of high temperature alloys such as nickel-cobalt, are coated with a thermal barrier coating (TBC) such as yttria-zirconia, and, if necessary, are internally cooled to help dissipate heat. The condition of the TBC is critical because spalling, where areas of the TBC peel or flake away from a vane or blade, can lead to vane or blade failure within hours. At present, machines are shut down at regular intervals and inspected, and damaged blades and vanes are then replaced. Condition monitoring of vanes and blades of operating machines until now has not been available, although gas monitoring has been proposed to look for particulates from the thermal barrier coating as an early warning system.

Typically, gas turbine machines have three or four rows of vanes and blades having a TBC and which are subjected to the most severe conditions. There may be, depending upon the type of machine, about 50 to 100 blades and vanes per row, and up to approximately 200–500 total blades and vanes having a TBC. Currently, it is necessary to periodically stop the turbine and inspect all of these components for deterioration of the coating or other defects. It would be desirable to determine the condition of the thermal barrier coating of these components while a gas turbine machine is in operation. Avoiding the need to periodically stop the turbine for inspection reduces downtime and increases turbine efficiency. Similarly, early detection of defects reduces repair costs and outage time, again increasing turbine efficiency. A need exists for monitoring the condition of the thermal barrier coating of blades and vanes within the turbine over time, while the turbine is in operation, to detect changes in the coating and deterioration thereof.

Various methods and systems for detecting and locating defects within a turbine engine or in turbine components have been proposed. For example, various pending applications of the current inventors cover methods of acoustic waveguide or radio frequency monitoring of turbines to detect deterioration in the coating or the presence of foreign objects in the turbine.

However, there is a continued need for new methods and apparatus for detecting the deterioration of the thermal barrier coating on blades and vanes in a combustion turbine, to provide an indication of when a turbine needs to be shut down for maintenance.

SUMMARY OF THE INVENTION

The present invention provides a method of monitoring the condition of a thermal barrier coating on turbine blades and/or vanes, while the turbine is in operation. The method comprises providing a means for receiving ultraviolet emissions from the blades or vanes during operation of the turbine and a means for transmitting the ultraviolet emissions to an ultraviolet sensor external to the turbine. The ultraviolet emissions are monitored over time to detect deterioration of the thermal barrier coating on the blades or vanes.

Ultraviolet emission magnitude, wavelength and pulse counts are expected to decrease in magnitude and number as the thermal barrier coating on the blades and vanes deteriorates, thus giving an indication of the condition of the thermal barrier coating.

It is an object of the present invention, therefore, to provide a method and apparatus for monitoring the condition of the thermal barrier coating on turbine blades and vanes using ultraviolet radiation sensors to detect changes in UV emissions and deterioration of the coating over time.

It is a further object of the invention to provide a method and apparatus for monitoring the condition of the thermal barrier coating of blades and vanes in gas turbines, by monitoring changes in UV emissions over time, while the turbine is in operation.

These and other objects of the invention will become more readily apparent from the following drawing, detailed description and appended claims.

BRIEF DESCRIPTION OF THE DRAWINGS

The invention is further illustrated by the following drawings in which.

DETAILED DESCRIPTION OF PREFERRED EMBODIMENTS

Figure 1:
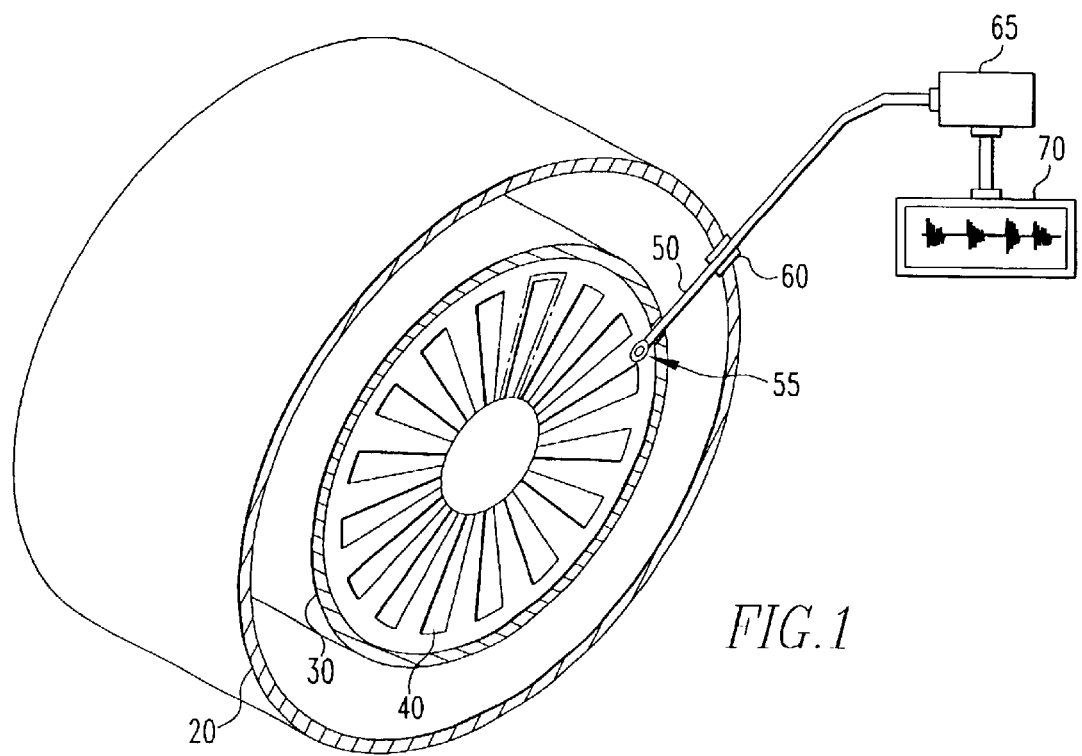
FIG. 1 is an internal view of a combustion turbine having the UV monitoring method and apparatus of the present invention.

Accordingly, the present invention provides a method of monitoring the condition of a thermal barrier coating on turbine blades and/or vanes, while the turbine is in operation. The method comprises providing a means for receiving ultraviolet emissions from the blades or vanes during operation of the turbine and a means for transmitting the ultraviolet emissions to an ultraviolet sensor external to the turbine. The ultraviolet emissions are monitored over time to detect deterioration of the thermal barrier coating on the blades or vanes.

The vanes and blades and associated protective thermal barrier coatings of gas turbine machines are subject to high pressure, high temperature and high velocity gas flow which is likely to create friction electricity (tribocharging) of the insulating yttria-zirconia TBC. In addition, because of the high temperature and pressure, charged particles (electrons and ions) are present in the gas flow as well as electrons generated by the friction electricity. As the thermal barrier coating is a dielectric (electrical insulator) the presence of electrons, ions and charged particles allows it to charge to high voltages which generate electrical discharges. Electrically insulating surfaces, such as those having a TBC, even though grounded, will be rapidly charging and discharging, so that electrical discharges (tiny sparks) will occur. These discharges have associated ultraviolet, radio frequency and ultrasonic emissions. The build-up of an electrical charge of about 20 kV on the TBC will be sufficient to generate electrical glow coronas and/or spark-type electrical discharges at narrow edges and ends of blades and vanes. An analogous situation occurs when the space shuttle reenters the earth's atmosphere, and air friction causes the shuttle to be enveloped in a corona glow or plasma sheath. It should be noted that even uncoated blades and vanes will have associated electrical discharges, though of a lower level than coated parts, due to the gas pressure differentials associated with blades and vanes. Thus, the UV monitoring system of the present invention can also be used to detect defects (e.g. chips or cracks) in uncoated blades or vanes.

A unique feature of electrical coronas in nitrogen (the main gas component in a combustion turbine) is the emission of ultraviolet (UV) radiation in the ~2000 to ~3000A wavelength, a wavelength below that which is radiated by the sun (~3650A). Monitoring the changes in UV radiation with time allows the condition of the TBC to be assessed, because as the TBC deteriorates, the total electrical charge, total corona glow and associated UV emissions will be reduced. The UV emissions can be viewed with a fish-eye-type of quartz (UV transparent) viewing port in the machine wall and transmitted outside the turbine via quartz fibers or sapphire rods for measurement. The UV levels and pulse repetition rate are then measured by a UV sensitive photomultiplier and oscilloscope; a photodiode and counter; or a commercial arc and flame sensor.

Due to tribocharging on the thermal barrier coating of the vanes and blades of gas turbine machines, a large high voltage electrical charge will build up on the yttria/zirconia TBC. This high voltage charge will be sufficient to electrically break down the high velocity (1000–2000 mph), high pressure (100–500 lb/in), high temperature (1000–2000° C.) gas/vapor mixture ($N_2$, $O_2$ and $H_2O$) passing the blades and vanes. An electrical charge of at least 20 kV will build up on the TBC of vanes and blades (for comparison purposes, combing one's hair on a dry day can yield 10 kV). This voltage will cause electrical glow or pulse-type coronas (electrical spark-type discharges) at the vane/blade edges. All of these coronas generate ultraviolet (UV) emissions in the far UV spectrum, i.e., in the ~2000A to ~3000A wavelength range.

As the TBC deteriorates with time in service, the electrical charge, electrical coronas and UV emissions will decrease in magnitude, or other characteristics, such as wavelength and pulse repetition rate, may change so that monitoring the levels of UV emissions can provide an indication of the condition of the TBC.

The UV emissions will be linked in time by the number of blades and vanes in a first row and by the machine revolutions per second. For example, with one UV pulse per blade(80 blades in the first row), with 80 pulses per machine revolution, the magnitude of the pulses should be substantially the same on newly coated blades. As the thermal barrier coating deteriorates, one or more blades will generate pulses which are not the same as the others, indicating a need for service.

Alternately, determining which blade requires servicing can be accomplished using a lens proximate to one vane, in conjunction with a "marking blade" designed to create a different ultraviolet emission than the other blades as it passes the lens. Such a marking blade may be produced by designing a coating intended to produce a greater ultraviolet emission, for example, by adding materials such as phosphors, which emit ultraviolet, blue or other light under electron bombardment. A blade requiring service will generate a different magnitude ultraviolet emission, wavelength or pulse repetition rate than the remaining blades. When viewing a sequence of ultraviolet emission signals, the number of signals between the marking blade and the blade generating a different magnitude signal can be used to determine the blade requiring service.

The means for receiving ultraviolet emissions will comprise quartz viewing ports which will be located in the machine walls in radial alignment with the blades or vanes being monitored. Exact alignment is not necessary, because the ultraviolet light rays will bounce off several surfaces to exit the port. The means for transmitting the UV emissions to a point external to the turbine will include, for example, high temperature, far UV transmitting fiber optics (about 150 nm to about 400 nm), such as quartz or sapphire. Suitable UV sensors include, but are not limited to, UV sensitive photomultipliers, photodiodes or commercial solar blind UV arc and flame sensors.

In another embodiment, the present invention provides an apparatus for monitoring the condition of a thermal barrier coating on turbine blades and/or vanes, while the turbine is in operation. The apparatus comprises a means for receiving ultraviolet emissions from the blades or vanes during operation of the turbine; a means for transmitting said ultraviolet emissions to an ultraviolet sensor external to the turbine; and a means for monitoring the ultraviolet emissions over time to detect deterioration of the thermal barrier coating on the blades or vanes. The means for monitoring ultraviolet emissions over time will typically comprise software programs and data analysis methods which can analyze the stored data and detect changes in the UV emissions over time.

A schematic of the proposed ultraviolet sensing system is given in FIG. 1, which shows an internal view of a gas turbine. There is an outer wall 20, an inner wall 30, and a row of thermal barrier coated turbine blades 40. An ultraviolet transmitting fiber 50 is placed within the inner wall 20 and is attached to an ultraviolet light gathering lens 55, preferably a fish-eye quartz or sapphire lens. The transmitting fiber extends through both the inner wall 20 and a pressure seal 60 in the outer wall 30 to a point external to the turbine, where it is connected to an ultraviolet sensitive photomultiplier, photodiode, arc sensor or other means 65 for receiving the transmission. The transmission is then displayed on a display means 70 such as an oscilloscope, pulse counter or other suitable display means. It is anticipated that ultraviolet emissions from first and second row coated blades will reach an ultraviolet light gathering lens in the machine inner wall at a thermocouple location. The thermocouple location is used for convenience; other locations for the lens can also be used.

Due to high velocity gas flow at the thermal barrier coating surfaces on blades and vanes, tribocharging will build up a sufficiently high voltage to electrically break down the gas mixture at vane or blade edges. This will initiate electrical glow coronas and/or electrical spark-type discharges which radiate ultraviolet emissions in the ~2000A to ~3000A wavelength range. The following calculations and technical information confirm that there will be an electrical discharge in the ultraviolet region:

Typical Machine Data:
501 FD MACHINE:

| FIRST STAGE | INLET | OUTLET |
|---|---|---|
| PRESSURE | ≈150–250 psia | ≈100–150 psia |
| TEMPERATURE | ≈2000–3000° F. | ≈1500–2500° F. |
| GAS/VAPOR MIXTURE: | | |
| $N_2$  NO  $CO_2$  $O_2$ | $H_2O$ | AR |
| 74.15%  trace  4.10  11.76 | 9.11 | 0.89 |
| TYPICAL VELOCITY OF GAS FLOW: | | 1000–2000 mph |

Electrical Voltage Charge Required on Thermal Barrier Coating Surface for Electrical Glow Coronas to Occur In order to estimate the voltage charge required on a thermal barrier coated blade to initiate glow coronas, the type of gas, pressure and temperature surrounding the blades must be taken into account. In addition, the sharpness of the blade edges and distance from ground (the machine wall, for example) must be considered. The blade tips are likely to be sharper than one millimeter in diameter and the tips may be less than one millimeter from the machine wall. Consequently, a conservative estimate of the glow corona inception voltage can be calculated based on one millimeter diameter wires spaced two centimeters. The following equations for calculation purposes are from GASEOUS CONDUCTORS, 1958, pp. 254, 256, by James Dillon Cobine.

For parallel wires, the critical corona gradient ($E_c$) in air for a visual corona to form is represented by the following formula (1):

$$E_c = 30 m \delta \left[ 1 + \frac{0.301}{\sqrt{\delta a}} \right] \text{kV/cm} \quad (1)$$

where m is an irregularity factor of ~0.8, a is the wire radius in cm, $\delta$ is the air density factor as given by formula (2):

$$\delta = \frac{3.92b}{273 + t} \quad (2)$$

where b is the air pressure in cm of mercury, and t is the temperature in ° C. The voltage $V_c$ at which a glow corona first appears can be calculated as shown in formula (3):

$$Vc = E_c \cdot a \cdot \ln\left(\frac{S}{a}\right) \quad (3)$$

where $E_c$ is the critical corona gradient, a is the wire radius in cm, and S is the wire space in cm.

Based on formulas (1), (2), and (3), and a gas turbine environment of 100 to 250 psia and a temperature of 1500 to 2500° F., it is calculated that the voltages needed to initiate glow coronas range from about ≈10 to 25 kV/cm.

(iii) Electrical Voltage Required on Thermal Barrier Coating for Electrical Spark Breakdown to Occur to Nearest Ground Surface It is thought that at voltages lower than that needed to initiate glow coronas at blade edges, the voltage charge may be sufficient to cause electrical spark breakdown at small gaps, such as at the TBC surface near cooling holes or at the blade tip (which may be only 8–30 mil from the machine wall).

Figure 2:
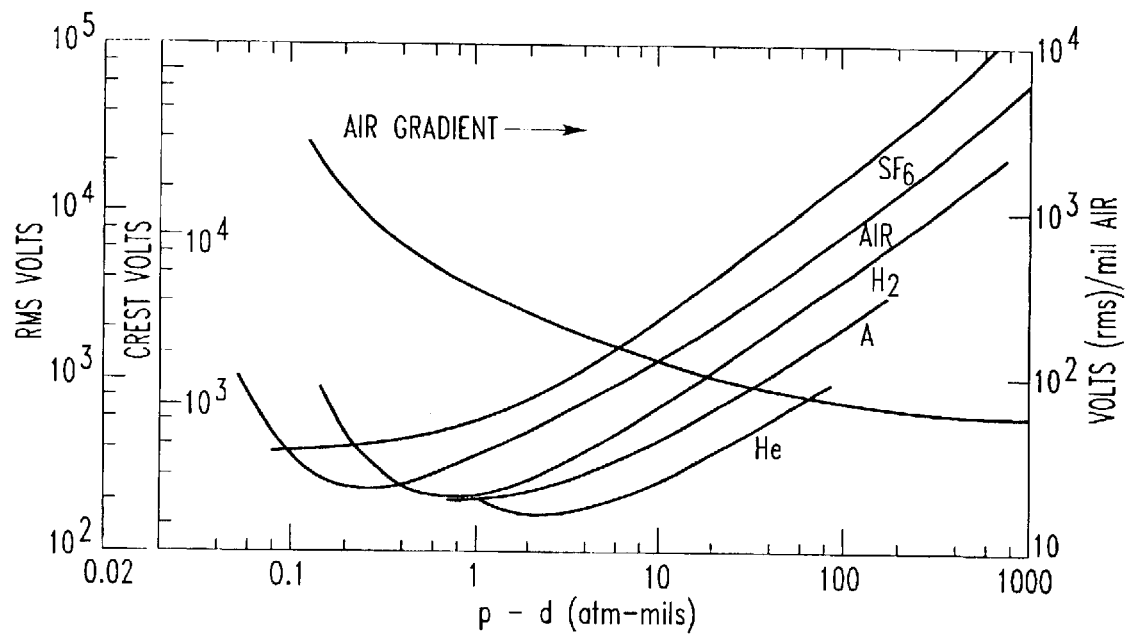
FIG. 2 illustrates the pressure-spacing dependence of the dielectric strength of gases known as Paschen's curves.

An estimate of the voltage required for spark-type breakdowns to occur can be made by assuming a 8–30 mil spark breakdown distance and using the Paschen Curve shown in FIG. 2 (from Krueger, F. H., "Partial Discharge Detection in High Voltage Equipment", Butterworths, 1989) for air. This curve gives breakdown voltage in relation to the product of gap spacing and air pressure (density takes into account temperature). Using an 8–30 mil spacing and pressures ranging from 100 to 250 psia from FIG. 2, the respective spark breakdown voltages are ~10 kV to ~25 kV.

These estimates of the voltages required to initiate glow coronas and/or spark breakdown are very modest, especially when considering that tribocharging from combing one's hair can yield 10 kV, and the space shuttle returning to earth is covered in a corona glow or plasma sheath due to air friction.

(iv) Ultraviolet Sensing of Corona Glow

As discussed previously the glow and spark coronas radiate ultraviolet emissions in the range of 2000 Å–3000 Å, which should be valuable for sensing purposes. Edison Ultraviolet Detectors have been commercially available for years and can sense ultraviolet emissions from tiny glow coronas and microsparks (4 mil gap). With this device, the ultraviolet emissions radiated from the flame of a match can be sensed at a distance of 80 feet in daylight and the ultraviolet emissions from a 4 mil spark gap at 50 feet.

Figure 3:
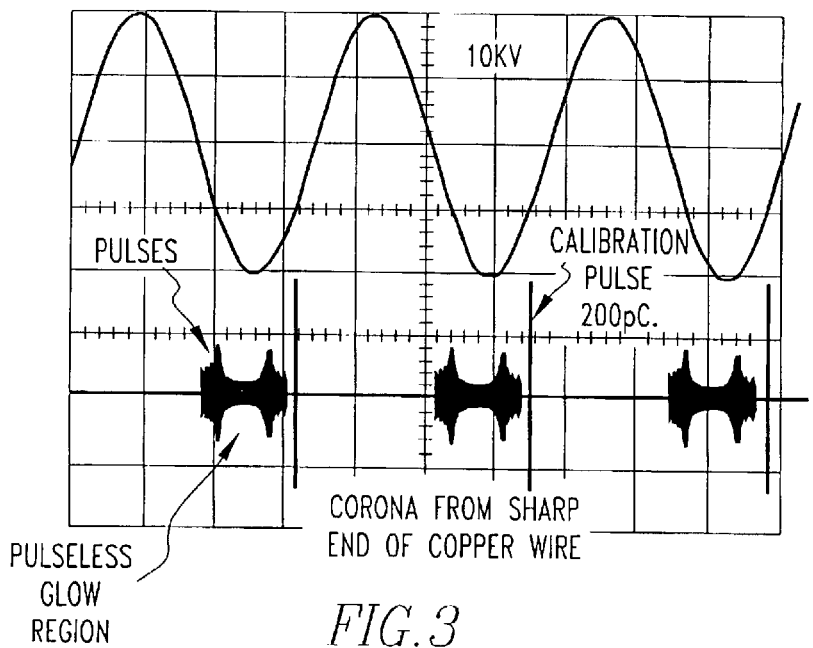
FIG. 3 shows the magnitude of negative glow to which an ultraviolet detector was sensitive at six inches.
Figure 4:
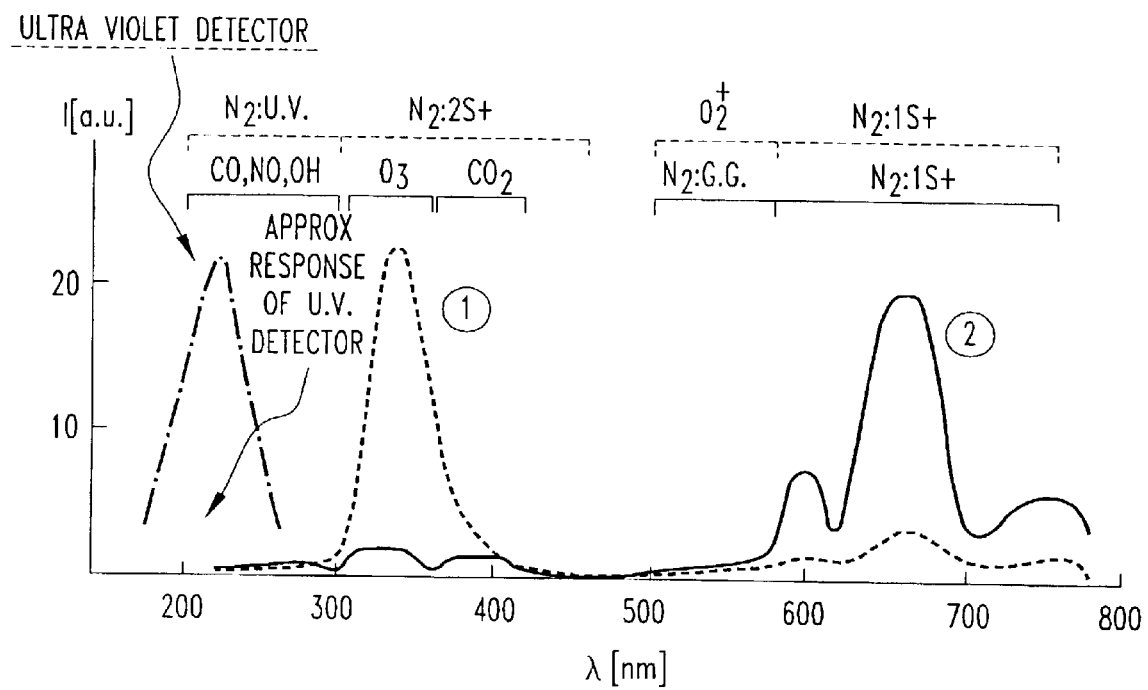
FIG. 4 shows the gross spectral variation of leader corona (1) and leader channel (2) light output.

The magnitude of the glow corona sensed and the ultraviolet sensing band (~1500 Å to ~2500 Å) of the Edison sensor is shown in FIG. 3 (previous Westinghouse document). FIG. 3 demonstrates that a simple ultraviolet sensor can detect emissions from glow coronas and associated electrical discharges of 20 to 80 picocoulombs in value. In a gas turbine engine, the electrical discharges are anticipated to be orders of magnitude larger. FIG. 4 shows light emitting bands from a very large, 10 meter long, spark (from G. Hartman, p. 62 of IEEE paper 74 CH 0910-0-PWR)

Whereas particular embodiments of this invention have been described above for purposes of illustration, it will be evident to those skilled in the art that numerous variations of the details of the present invention may be made without departing from the invention as defined in the appending claims.

What is claimed is:

1. A method of monitoring the condition of a thermal barrier coating on a turbine blade or vane comprising:
    providing a means for receiving ultraviolet emissions from said blade or said vane during operation of said turbine; and
    monitoring said ultraviolet emissions over time to detect deterioration of said thermal barrier coating on said blade or said vane.

2. The method of claim 1, further comprising a means for transmitting said ultraviolet emissions to an ultraviolet sensor external to said turbine.

3. The method of claim 1, wherein said means for receiving said ultraviolet emissions comprise an ultraviolet light gathering lens.

4. The method of claim 2, wherein said means for transmitting said ultraviolet emissions comprise ultraviolet transmitting fiber optics.

5. The method of claim 2, wherein said ultraviolet sensor is selected from the group consisting of ultraviolet sensitive photomultiplier, photodiode and arc/flame sensor.

6. The method of claim 1, further comprising monitoring said ultraviolet emissions over time to detect a reduction in said ultraviolet emissions.

* * * * *